US012715951B2

(12) United States Patent
Noguchi et al.

(10) Patent No.: US 12,715,951 B2
(45) Date of Patent: Aug. 25, 2026

(54) GRAFT POLYMER

(71) Applicant: DAIKIN INDUSTRIES, LTD., Osaka (JP)

(72) Inventors: Daisuke Noguchi, Osaka (JP); Tetsuya Uehara, Osaka (JP); Shinichi Minami, Osaka (JP); Teruyuki Fukuda, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 646 days.

(21) Appl. No.: 18/188,044

(22) Filed: Mar. 22, 2023

(65) Prior Publication Data

US 2023/0227596 A1 Jul. 20, 2023

Related U.S. Application Data

(63) Continuation of application No. PCT/JP2021/034866, filed on Sep. 22, 2021.

(30) Foreign Application Priority Data

Sep. 24, 2020 (JP) ................................ 2020-160115

(51) Int. Cl.
*C08F 285/00* (2006.01)
*A61K 8/73* (2006.01)
*C08F 2/10* (2006.01)

(52) U.S. Cl.
CPC ............ *C08F 285/00* (2013.01); *A61K 8/732* (2013.01); *C08F 2/10* (2013.01); *C08F 2810/40* (2013.01)

(58) Field of Classification Search
CPC ...... C08F 251/00; C08F 251/02; D21H 21/16
See application file for complete search history.

(56) References Cited

U.S. PATENT DOCUMENTS 4,791,063 A 12/1988 Hou et al.
2013/0272989 A1* 10/2013 Lee ........................ A61K 8/731 424/70.13
2021/0108371 A1* 4/2021 Oshima .................. D21H 19/16
2021/0164165 A1 6/2021 Yamamoto et al.

FOREIGN PATENT DOCUMENTS

CN 102660902 A 9/2012
JP 49-032925 A 3/1974
JP 60-500539 A 4/1985
JP 61-185517 A 8/1986
JP 01-203411 A 8/1989
JP 2011-202022 A 10/2011
JP 2014-239722 A 12/2014
TW 202030399 A 8/2020
WO WO-2020004639 A1 * 1/2020 ............ D21H 27/10

OTHER PUBLICATIONS

Chen, J. Appl. Polym. Sci. 2013, 2377-2382 (Year: 2013).*
Liu, Polym. Chem. 2014, 5, 3170-3181 (Year: 2014).*
International Preliminary Report on Patentability with a translation of the Written Opinion dated Mar. 28, 2023 in corresponding International Application No. PCT/JP2021/034866.
International Search Report for PCT/JP2021/034866, dated Dec. 7, 2021.
Extended European Search Report dated Sep. 23, 2024 in Application No. 21872514.1.

* cited by examiner

*Primary Examiner* — Robert C Boyle
(74) *Attorney, Agent, or Firm* — Sughrue Mion, PLLC

(57) ABSTRACT

An oil-resistant agent including a graft polymer obtained by graft modification of a bio-based material with a long-chain hydrocarbon group-containing non-fluorine polymer having a long-chain hydrocarbon group having 7 to 40 carbon atoms. Also disclosed is a fiber product including the graft polymer in the oil-resistant agent and a method for producing the oil-resistant agent.

12 Claims, No Drawings

GRAFT POLYMER

CROSS REFERENCE TO RELATED APPLICATIONS

This application is a Rule 53(b) Continuation of International Application No. PCT/JP2021/034866 filed Sep. 22, 2021, which claims priority based on Japanese Patent Application No. 2020-160115 filed Sep. 24, 2020, the respective disclosures of all of the above of which are incorporated herein by reference in their entirety.

TECHNICAL FIELD

The present disclosure relates to a graft polymer, in particular, a graft polymer that can be suitably used for an oil-resistant agent.

BACKGROUND ART

As an alternative to disposable plastic containers, paper containers are being expected. Food packaging materials and food containers made of paper are required to prevent exuding of moisture and an oil derived from food, and an oil-resistant agent is applied to paper by internal sizing or external sizing. In addition, in view of considering the environment, need for biodegradable materials or bio-based materials is also increasing.

Patent Literature 1 discloses a starch graft polymer that can be obtained by reacting cationic starch and a monomer containing (meth)acrylamide.

CITATION LIST

Patent Literature

Patent Literature 1: JP2011-202022A

SUMMARY

One embodiments of the present disclosure is as follows:

A graft polymer obtained by graft modification of a bio-based material with a long-chain hydrocarbon group-containing polymer having a long-chain hydrocarbon group having 7 to 40 carbon atoms.

DESCRIPTION OF EMBODIMENTS

In Patent Literature 1, there is no description of high-temperature oil resistance. High-temperature oil resistance is an important characteristic in products that are intended to be used at high temperatures (for example, food packaging materials). The present disclosure relates to an oil-resistant agent that is made from a bio-based material and capable of imparting high-temperature oil resistance.

The graft polymer in the present disclosure is capable of imparting excellent oil resistance and/or water resistance to substrates and, in particular, is capable of imparting high-temperature oil resistance to substrates. The graft polymer in the present disclosure is derived from a bio-based material and thus gives a small load to the environment.

<Graft Polymer>

A graft polymer is a compound obtained by the graft modification of a bio-based material with a polymer having a long-chain hydrocarbon group having 7 to 40 carbon atoms.

The polymer may be a non-fluorine polymer.

[Long-Chain Hydrocarbon Group]

The number of carbon atoms in the long-chain hydrocarbon group may be 7 or more, 10 or more, 12 or more, 14 or more, 16 or more, 18 or more or 20 or more and is preferably 10 or more or 12 or more. The number of carbon atoms in the long-chain hydrocarbon group may be 40 or less, 35 or less, 30 or less, 25 or less, 22 or less, 20 or less or 18 or less. The number of carbon atoms is preferably 30 or less.

The long-chain hydrocarbon group is preferably an aliphatic hydrocarbon group and more preferably a monovalent aliphatic hydrocarbon group. The long-chain hydrocarbon group may be linear, branched or cyclic, and is preferably linear. The long-chain hydrocarbon group may be unsaturated (for example, monounsaturated, diunsaturated, triunsaturated, tetraunsaturated or polyunsaturated) or saturated, and is, for example, an alkyl group.

Specific examples of the long-chain hydrocarbon group include alkyl groups such as an octyl group, a lauryl group, a palmityl group, a stearyl group, a behenyl group, a 2-ethylhexyl group and an isostearyl group; alkenyl groups such as an oleyl group, a palmitoyl group and an eicosenyl group; and the like.

[Amide Group]

The graft polymer may have an amide group. It is not necessary for the amide group that the amide group should bond to carbon atoms at both ends thereof, and the amide group may be an amide group that is a part of a urethane group or a urea group. The amide group may be a carboxylic amide or a sulfonamide. The amide group is preferably adjacent to the long-chain hydrocarbon group.

[Long-Chain Hydrocarbon Amide Group]

The graft polymer preferably has a long-chain hydrocarbon amide group. The long-chain hydrocarbon amide group may be at least one long-chain hydrocarbon amide group selected from the group consisting of

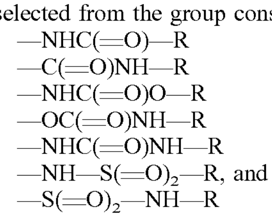

—NHC(=O)—R

—C(=O)NH—R

—NHC(=O)O—R

—OC(=O)NH—R

—NHC(=O)NH—R

—NH—S(=O)$_2$—R, and

—S(=O)$_2$—NH—R wherein each R is independently a long-chain hydrocarbon group having 7 to 40 carbon atoms.

R may be the same as the above-described long-chain hydrocarbon group.

[Bondable Group]

The graft polymer preferably has a bondable group that is capable of chemically or physically bonding to a functional group in a substrate (for example, a hydroxy group of cellulose in paper). The chemical bond refers to, for example, a covalent bond. The physical bond refers to, for example, an ionic bond, a hydrogen bond or the like. The bondable group may be derived from the bio-based material. When the graft polymer has the bondable group, the graft polymer is highly fixed to cellulose, and the oil resistance and/or water-repellency of paper products can be favorably developed. The bondable group is normally derived from a bio-based material.

The bondable group is, in particular, a polar group and, in particular, a polar group other than an amide group. Examples of the polar group include active hydrogen-containing groups, active hydrogen-reactive groups, cation-donating group-containing groups, anion-donating groups and the like. Specific examples of the polar group include a hydroxy group, an amino group, a thiol group, a hydrazide group, melamine, an aldehyde group, an epoxy group, a (blocked) isocyanate group, a urea group, a urethane group, a halogen group, a carboxylic acid group, a sulfonic acid group, a phosphoric acid group, an ammonium group and the like. In the case where the polar group can form an ion, the polar group may be in the form of a conjugate base or conjugate acid thereof.

[Amount and Others of Amide Group]

The content of the long-chain hydrocarbon group in the graft polymer may be 1% by weight or more, 3% by weight or more, 5% by weight or more, 10% by weight or more, 20% by weight or more or 30% by weight or more and is preferably 5% by weight or more. The content of the long-chain hydrocarbon group in the graft polymer may be 80% by weight or less, 70% by weight or less, 60% by weight or less, 50% by weight or less, 40% by weight or less, 30% by weight or less or 25% by weight or less and is preferably 70% by weight or less.

The content of the amide group in the graft polymer may be 0.5% by weight or more, 1% by weight or more, 3% by weight or more, 5% by weight or more or 10% by weight or more and is preferably 1% by weight or more. The content of the amide group in the graft polymer may be 30% by weight or less, 20% by weight or less, 10% by weight or less, 5% by weight or less, 1% by weight or less or 0.5% by weight or less and is preferably 10% by weight or less. Here, the content of the amide group in the graft polymer means the weight proportion of NHC(═O) moieties in the graft polymer.

The content of the bondable group in the graft polymer may be 0.5% by weight or more, 1% by weight or more, 3% by weight or more, 5% by weight or more, 10% by weight or more or 20% by weight or more and is preferably 3% by weight or more. The content of the bondable group in the amide compound may be 70% by weight or less, 50% by weight or less, 30% by weight or less, 20% by weight or less, 10% by weight or less or 5% by weight or less and is preferably 30% by weight or less.

[Biobased Content]

The biobased content according to ASTM D6866 of the graft polymer may be 50% or more, 60% or more, 70% or more, 80% or more, 90% or more, 95% or more and is preferably 80% or more and more preferably 95% or more. The fact that the biobased content is high means that the amount of a fossil resource-based material used, which is typified by petroleum or the like, is small. From such a viewpoint, it can be said that the biobased content of the graft polymer is preferably as high as possible.

[Bio-Based Material]

"Bio-based material" refers to a material derived from a biomolecule of an animal, a plant, a microbe or the like. It is known in the technical field that carbon 14 (C-14), which has a half-life of approximately 5,700 years, occurs in bio-based materials, but does not occur in fossil fuels. Therefore, "bio-based material" may mean an organic material in which carbon is derived from a biological source other than fossils.

The bio-based material may be a low-molecular material (for example, the molecular weight is 1,000 or less or 500 or less) or may be a polymer (natural polymer). In a case where the bio-based material is a polymer, the weight-average molecular weight thereof may be 1,000 or more, 3,000 or more, 5,000 or more, 7,500 or more, 10,000 or more, 30,000 or more, 100,000 or more, 300,000 or more or 500,000 or more. The weight-average molecular weight of the polymer may be 10,000,000 or less, 1,000,000 or less, 7,500,000 or less, 500,000 or less, 300,000 or less, 100,000 or less, 75,000 or less or 50,000 or less.

Normally, the bio-based material has a polar group. Examples of the polar group include a hydroxy group, an amino group, a carboxylic acid group and the like.

Examples of the bio-based material include sugar, alcohols, amino acids, peptide compounds, nucleobases, nucleic acids, alkaloid compounds, steroid compounds, hormones, polyphenols, vitamins and the like.

Specific examples of the sugar compound include glucose, sucrose, galactose, lactose, dextrose, erythritol, maltitol, sorbitol, xylitol, mannitol, isomaltol, lactitol, glycerol carboxyalkyl polysaccharides, carboxymethyl cellulose, chitin, chitosan, levan, pullulan, curdian, xanthan, carrageenan, locust bean gum, pectin, dextrin, starch, guar gum, alginic acid, lignin and the like.

Specific examples of the alcohols include glycerin, propylene glycol, 1,3-butylene glycol, polyethylene glycol, sorbitol (sugar alcohol), xylitol (sugar alcohol) and the like.

Specific examples of the amino acids or the peptides include a variety of enzymes such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, collagen, polypeptide, protease, lipase, oxygenase and peroxidase and the like.

Specific examples of the nucleobases or the nucleic acids include uracil, adenine, guanine, cytosine, thymine, nucleotides, deoxyribonucleic acid (DNA), ribonucleic acid (RNA) and the like.

Specific examples of a fatty acid or fats and oils include butyric acid, valeric acid, caproic acid, enanthic acid, capric acid, pelargonic acid, capric acid, lauric acid, myristic acid, pentadecylic acid, palmitic acid, palmitoleic acid, margaric acid, stearic acid, oleic acid, vaccenic acid, α-linolenic acid, linoleic acid, γ-linolenic acid, eleostearic acid, arachidic acid, mead acid, arachidonic acid, behenic acid, lignoceric acid, nervonic acid, cerotic acid, montanic acid, melissic acid, fatty acid esters thereof, vegetable fats and oils such as candelilla wax, carnauba wax, rice wax, wood wax and jojoba solid wax, animal fats and oils such as beeswax, lanolin and spermaceti and the like.

Other specific examples of the bio-based material include isoflavone, proanthocyanidin, anthocyanin, catechin, rutin, hesperidin, tannin, ellagic acid, lignan, curcumin, coumarin, sweet tea polyphenol, chlorogenic acid, resveratrol, rose polyphenol, astaxanthin, lutein, fucoxanthin, zeaxanthin, beta cryptoxanthin and the like.

(Sugar)

The bio-based material may be sugar. Examples of the sugar include monosaccharides, oligosaccharides, polysaccharides, sugar alcohols, starch and the like.

Monosaccharides are, among sugar, basic substances that do not become a simpler molecule by hydrolysis and the constituent unit of oligosaccharides or polysaccharides. Monosaccharides may be compounds represented by the following general formula:

$$C_nH_{2n}O_n$$

wherein the number of carbon atoms (n) is 2, 3, 4, 5, 6, 7, 8, 9 and 10 (they can be referred to as a diose, a triose, a tetrose, a pentose, a hexose, a heptose, an octose, a nonose and a decose, respectively). Monosaccharides are classified into aldoses, which have an aldehyde group, and ketoses, which have a ketone group. Since monosaccharides with n=3 or more have asymmetric carbon atoms, a number of stereoisomers can occur depending on the number of asymmetric carbon atoms, and naturally-known monosaccharides are some of the stereoisomers. Naturally occurring monosaccharides are often pentoses and hexoses. As monosaccharides that are used in the present disclosure, aldoses, which are aldehydes of a chain polyhydric alcohol with n=5 or more, are preferable since aldoses occur in nature in large quantities. Examples of such monosaccharides include glucose, mannose, galactose, xylose and the like, and, among them, glucose and galactose are more preferable. Monosaccharides can be each used singly or two or more monosaccharides can be used in combination.

Sugar alcohols are polyhydroxy alkanes that are obtained by reducing an aldose or a ketose. As sugar alcohols that are used in the present disclosure, chain polyhydric alcohols are preferable.

Such sugar alcohols may be compounds represented by the following general formula:

$$C_nH_{2n+1}O_n$$

wherein n is 3, 4, 5, 6, 7, 8, 9 and 10 (they can be referred to as a tritol, a tetrytol, a pentitol, a hexitol, a heptitol, an octitol, a nonitol and a decitol). As each sugar alcohol, a number of stereoisomers occur depending on the number of asymmetric carbon atoms. In the present disclosure, sugar alcohols with n=3 to 6 are preferably used. Specific examples of sugar alcohols include sorbitol, mannitol, dulcitol, xylitol, erythritol, glycerin and the like. Sugar alcohols can be each used singly or two or more monosaccharides can be used in combination.

Sugar having a structure in which two or more and up to approximately 10 monosaccharides are bonded to one another by glycoside bonds are referred to as oligosaccharides. Oligosaccharides are classified into disaccharides, trisaccharides, tetrasaccharides, pentasaccharides and the like depending on the number of monosaccharides. Specific examples thereof include sucrose, lactose, trehalose, cellobiose, maltose, raffinose, stachyose and the like. These oligosaccharides with an alcoholized terminal (terminal-alcoholized oligosaccharides) can also be used.

Polysaccharides are a collective term of polymer compounds in which monosaccharides are polyglycosylated (for example, with a degree of polymerization of 10 or more), and referred to as homopolysaccharides (homoglycans) when composed of one kind of saccharide or heteropolysaccharides (heteroglycans) when composed of two or more kinds of saccharides. Polysaccharides widely occur in the animal, plant and microbial worlds as storage polysaccharides (starch and the like), structural polysaccharides (cellulose and the like) and functional polysaccharide (heparin and the like).

Polysaccharides mainly contain an aldohexose and an aldopentose as constituent units and are polymer compounds in which the aldopentose and the aldohexose are connected to each other in a linear, branched or cyclic manner by a glycoside bond. The aldohexose and the aldopentose form a six-membered ring structure, which is referred to as a pyranose ring, by an intramolecular hemiacetal bond between an aldehyde at the C1 position and an alcohol at the C5 position. An aldohexose and an aldopentose in a natural polysaccharide molecule mainly have such pyranose ring structure. Also included are a sulfate ester, a phosphate ester, other organic acid esters or methyl ether of aldohexose sugar, which is a constituent unit of natural polysaccharides; an uronic acid in which only a first alcohol is oxidized to a carboxyl group; a hexosamine in which a hydroxy group at the C2 position of an aldohexose is substituted by an amino group, and N-acetyl hexosamine as a derivative thereof; and 3,6-anhydrous aldohexose in which an ether is formed between hydroxy groups at the C3 position and at the C6 position. Natural polysaccharides are widely distributed in the animal and plant worlds, and occur in plants as a cell wall constituent of higher plants or seaweed, and a component that is not involved in the constitution of a cell wall in higher plants or seaweed, or as a cell constituent of microbes. Examples of the component that is not involved in the constitution of a cell wall of higher plants or seaweed include a viscous substance that is contained in a cell fluid or a storage substance such as starch. Natural polysaccharides occur in animals as a storage substance such as glycogen or a constituent of a viscous fluid such as heparin or chondroitin sulfate. When classified according to the constituent, natural polysaccharides are classified into neutral polysaccharides, acidic polysaccharides and basic polysaccharides. As the heteropolysaccharides, heteropolysaccharides composed of a hexose alone are contained in amorphophallus konjac, gualan or the like, and heteropolysaccharides composed of a pentose alone are contained in xylan, araboxylan or the like. As heteropolysaccharides containing a hexose and a pentose, tamarind, *Actinidia rufa* and the like are known. Regarding the acidic polysaccharides, *Abelmoschus manihot*, pectin and the like are mentioned as examples of acidic polysaccharides containing only a uronic acid and acidic polysaccharides containing galacturonic acid and a neutral polysaccharide; *Matricaria recutita, Asparagus cochinchinensis* and the like are mentioned as examples of acidic polysaccharides containing glucuronic acid and a neutral polysaccharide; and acidic polysaccharides containing a sulfate ester, a phosphate ester, an organic acid ester or methyl ether of a neutral polysaccharide or a 3,6-anhydride are mentioned as other examples. Regarding the basic polysaccharides, basic polysaccharides containing glucosamine or galactosamine as a constituent monosaccharide are mentioned as examples thereof. In addition to these natural polysaccharides, examples of polysaccharides used in the present disclosure include polysaccharides obtained by hydrolyzing the natural polysaccharide, by optionally heating, with an organic acid or an inorganic acid or, furthermore, a hydrolysis enzyme of the natural polysaccharides as catalysts in a solid phase, a liquid phase or a solid-liquid mixed phase; and polysaccharides obtained by further processing the natural polysaccharides or the product of the above-described hydrolysis of the natural polysaccharides. The weight-average molecular weight of starch may be 1,000 to 10,000,000, preferably 5,000 to 7,500,000 or more and more preferably 7,500 to 5,000,000 or less.

Starch is encompassed by the polysaccharides, and starch that is used in the present disclosure will be described in more detail below. Regarding the starch that is used in the present disclosure, not only raw starch (unmodified starch) such as wheat starch, corn starch, mochi corn starch, potato starch, tapioca starch, rice starch, sweet potato starch and sago starch, but also a variety of processed starch are mentioned as examples thereof. Examples of the processed starch include physically modified starch such as alpha starch, isolated purified amylose, isolated purified amylopectin and wet-heat-treated starch, hydrolyzed dextrin, enzyme-degraded dextrin, enzyme-modified starch such as those modified with amylose, acid-treated starch, chemical decomposition-modified starch such as hypochlorous acid-oxidized starch and dialdehyde starch, chemically modified starch such as esterified starch (acetic acid-esterified starch, succinic acid-esterified starch, nitric acid-esterified starch, phosphoric acid-esterified starch, urea phosphoric acid-esterified starch, xanthogenic acid-esterified starch, acetoacetic acid-esterified starch and the like), etherified starch (allyl etherified starch, methyl etherified starch, carboxymethyl etherified starch, hydroxyethyl etherified starch, hydroxypropyl etherified starch and the like), cationized starch (a reaction product of starch and 2-diethylaminoethyl chloride, a reaction product of starch and 2,3-epoxypropyltrimethylammonium chloride, and the like) and cross-linked starch (formaldehyde cross-linked starch, epichlorohydrin cross-linked starch, phosphoric acid cross-linked starch, acrolein cross-linked starch and the like), grafted starch obtained by graft-polymerizing a monomer to a variety of starches [examples of the monomer include vinyl acetate, vinyl propionate, t-butyl vinyl ether, (meth)acrylamide, (meth)acrylic acid, (meth)acrylic acid alkyl ester, (meth)acrylic acid hydroxyalkyl ester, (meth)acrylic acid ethoxyalkyl ester, (meth)acrylic acid methoxypolyethylene glycol ester, (meth)acrylic acid 2-hydroxy-3-chloropropyl ester, (meth)acrylic acid dimethylaminoethyl ester, glycidyl methacrylate ester, acrylonitrile, styrene, maleic anhydride, itaconic acid and the like] and the like. Among these starch, processed starch that is soluble in water is preferable. Starch may be a water-containing product. These starches can be each used singly or two or more kinds of starch can be used in combination.

[Structure and Others of Graft Polymer]

The graft polymer is a graft polymer obtained by the graft modification of the bio-based material with a long-chain hydrocarbon group-containing polymer having a long-chain hydrocarbon group. The graft polymer includes both a trunk moiety derived from the bio-based material and a branch moiety (extended moiety, or graft) that is the long-chain hydrocarbon group-containing polymer and attached to the trunk moiety.

The long-chain hydrocarbon group-containing polymer has a repeating unit that is formed of an acrylic monomer (a) having a long-chain hydrocarbon group having 7 to 40 carbon atoms, and the acrylic monomer (a) may contain at least one of an amide monomer (a1) and a non-amide monomer (a2). The acrylic monomer (a) may contain any one of the monomers (a1) and (a2) or may contain both of (a1) and (a2).

The long-chain hydrocarbon group-containing polymer may have a repeating unit that is formed of an acrylic monomer (b) having a hydrophilic group. The long-chain hydrocarbon group-containing polymer may have a repeating unit that is formed of a monomer (c) having an ion donor group. The long-chain hydrocarbon group-containing polymer may have a repeating unit that is formed of a further monomer (d) other than the monomers (a) to (c).

(a) Monomer Having Long-Chain Hydrocarbon Group

The monomer (a) having a long-chain hydrocarbon group is preferably a monomer represented by

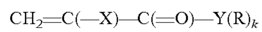

$$CH_2{=}C(-X)-C(=O)-Y(R)_k$$

wherein R is each independently a hydrocarbon group having 7 to 40 carbon atoms, X is a hydrogen atom, a monovalent organic group or a halogen atom, Y is a group composed of at least one selected from a divalent to tetravalent hydrocarbon group having one carbon atom (in particular, —$CH_2$— or —CH═), —$C_6H_4$—, —O—, —C(═O)—, —$S(=O)_2$— or —NH—, and k is 1 to 3.

X may be a hydrogen atom, a methyl group, a halogen, a substituted or unsubstituted benzyl group or a substituted or unsubstituted phenyl group. Examples of X include a hydrogen atom, a methyl group, a chlorine atom, a bromine atom, an iodine atom, a fluorine atom and a cyano group. X is preferably a hydrogen atom, a methyl group or a chlorine atom. X is particularly preferably a hydrogen atom.

Y is a divalent to tetravalent group. Y is preferably a divalent group.

Y is preferably a group composed of at least one selected from a hydrocarbon group having one carbon atom, —$C_6H_4$—, —O—, —C(═O)—, —$S(=O)_2$— or —NH—. Examples of the hydrocarbon group having one carbon atom include —$CH_2$—, —CH═, which has a branched structure, and —C≡, which has a branched structure.

Y may be —Y'—, —Y'—Y'—, —Y'—C(═O)—, —C(═O)—Y'—, —Y'—C(═O)—Y'—, —Y'—R'—, —Y'—R'—Y'—, —Y'—R'—Y'—C(═O)—, —Y'—R'—C(═O)—Y'—, —Y'—R'—Y'—C(═O)—Y'— or —Y'—R'—Y'—R'— wherein Y' is a direct bond, —O—, —NH— or —$S(=O)_2$—, and R' is —$(CH_2)_m$— (m is an integer of 1 to 5) or —$C_6H_4$— (phenylene group)

Specific examples of Y include —O—, —NH—, —O—C(═O)—, —C(═O)—NH—, —NH—C(═O)—, —O—C(═O)—NH—, —NH—C(═O)—O—, —NH—C(═O)—NH—, —O—$C_6H_4$—, —O—$(CH_2)_m$O—, —NH—$(CH_2)_m$—NH—, —O—$(CH_2)_m$—NH—, —NH—$(CH_2)_m$—O—, —O—$(CH_2)_m$—O—C(═O)—, —O—$(CH_2)_m$—C(═O)—O—, —NH—$(CH_2)_m$—O—C(═O)—, —NH—$(CH_2)_m$—C(═O)—O—, —O—$(CH_2)_m$—O—C(═O)—NH—, —O—$(CH_2)_m$—NH—C(═O)—O—, —O—$(CH_2)_m$C(═O)—NH—, —O—$(CH_2)_m$—NH—C(═O)—, —O—$(CH_2)_m$—NH—C(═O)—NH—, —O—$(CH_2)_m$—O—$C_6H_4$—, —O—$(CH_2)_m$—NH—$S(=O)_2$—, —O—$(CH_2)_m$—$S(=O)_2$—NH—, —NH—$(CH_2)_m$—O—C(═O)—NH—, —NH—$(CH_2)_m$—NH—C(═O)—O—, —NH—$(CH_2)_m$—C(═O)—NH—, —NH—$(CH_2)_m$—NH—C(═O)—, —NH—$(CH_2)_m$—NH—C(═O)—NH—, —NH—$(CH_2)_m$—O—$C_6H_4$—, —NH—$(CH_2)_m$—NH—$C_6H_4$—, —NH—$(CH_2)_m$—NH—$S(=O)_2$—, or —NH—$(CH_2)_m$—$S(=O)_2$—NH—, wherein m is 1 to 5 and particularly 2 or 4.

Y is preferably —O—, —NH—, —O—$(CH_2)_m$—O—C(═O)—, —O—$(CH_2)_m$—NH—C(═O)—, —O—$(CH_2)_m$O—C(═O)—NH—, —O—$(CH_2)_m$—NH—C(═O)—O—, —O—$(CH_2)_m$—NH—C(═O)—NH—, —O—$(CH_2)_m$—NH—$S(=O)_2$—, —O—$(CH_2)$m-$S(=O)_2$—NH—, —NH—$(CH_2)_m$—NH—$S(=O)_2$—, or —NH—$(CH_2)_m$—$S(=O)_2$—NH—, wherein m is an integer of 1 to 5 and particularly 2 or 4. Y is more preferably —O— or —O—$(CH_2)_m$—NH—C(═O)—, particularly, —O—$(CH_2)_m$—NH—C(═O)—. Y is preferably not a hydrocarbon group.

R is a long-chain hydrocarbon group and, preferably an aliphatic hydrocarbon group, especially preferably a saturated long-chain hydrocarbon group and, particularly preferably an alkyl group. The number of carbon atoms in the long-chain hydrocarbon group may be 7 or more, 10 or more, 12 or more, 14 or more, 16 or more, 18 or more or 20 or more and is preferably 10 or more or 12 or more. The number of carbon atoms in the long-chain hydrocarbon group may be 40 or less, 35 or less, 30 or less, 25 or less, 22 or less, 20 or less or 18 or less. The number of carbon atoms is preferably 30 or less.

Amide Monomer (a1)

The amide monomer (a1) has a long-chain hydrocarbon group and an amide group. The long-chain hydrocarbon group and the amide group are as described above.

The amide monomer (a1) is a (meth)acrylate or (meth) acrylamide having a long-chain hydrocarbon group and an amide group and optionally further having a group composed of at least one selected from —O—, —C(═O)—, $—S(=O)_2—$ or —NH—. Herein, "(meth)acryl" means acryl or methacryl. For example, "(meth)acrylate" means an acrylate or a methacrylate. The atom on the α position in an acrylate is not limited to a hydrogen atom and may be a different group.

Amide monomer (a1) may be a compound having at least one amide group and represented by the formula:

$$CH_2=C(—X^1)—C(=O)—Y^1—Z(—Y^2—R^1)_n$$

wherein $R^1$ is each independently a long-chain hydrocarbon group having 7 to 40 carbon atoms, $X^1$ is a hydrogen atom, a monovalent organic group or a halogen atom, $Y^1$ is —O— or —NH—, $Y^2$ is each independently a group composed of at least one selected from a direct bond, —O—, —C(=O)—, $—S(=O)_2—$ or —NH—, Z is a direct bond or a divalent or trivalent hydrocarbon group having 1 to 6 carbon atoms (for example, 1 to 5, 1 to 4, or 1 to 3), and n is 1 or 2.

$R^1$ is a long-chain hydrocarbon group and, preferably an aliphatic hydrocarbon group, especially preferably a saturated long-chain hydrocarbon group and, particularly preferably an alkyl group. The number of carbon atoms in the long-chain hydrocarbon group may be 7 or more, 10 or more, 12 or more, 14 or more, 16 or more, 18 or more or 20 or more and is preferably 10 or more or 12 or more. The number of carbon atoms in the long-chain hydrocarbon group may be 40 or less, 35 or less, 30 or less, 25 or less, 22 or less, 20 or less or 18 or less. The number of carbon atoms is preferably 30 or less.

$X^1$ may be a hydrogen atom, a methyl group, a halogen atom (for example, F, Cl, Br or I (for example, a fluorine atom may be excluded)), a substituted or unsubstituted benzyl group or a substituted or unsubstituted phenyl group. A hydrogen atom, a methyl group or a chlorine atom is preferable.

$Y^1$ may be —Y'—, —Y'—Y'—, —Y'—C(=O)—, —C(=O)—Y'—, —Y'—C(=O)—Y'—, —Y'—R'—, —Y'—R'—Y'—, —Y'—R'—Y'—C(=O)—, —Y'—R'—C(=O)—Y'—, —Y'—R'—C(=O)—Y'—, —Y'—R'—Y'—C(=O)—Y'— or —Y'—R'—Y'—R'— wherein Y' is each independently a direct bond, —O—, —NH— or $—S(=O)_2—$,

R' is $—(CH_2)_m—$ (m is an integer of 1 to 5), a linear hydrocarbon group having an unsaturated bond having 1 to 5 carbon atoms, a hydrocarbon group having a branched structure having 1 to 5 carbon atoms or $—(CH_2)_1—C_6H_4—(CH_2)_1—$ (l is each independently an integer of 0 to 5, and $—C6H_4—$ is a phenylene group)

Specific examples of $Y^2$ include a direct bond, —O—, —NH—, —O—C(=O)—, —C(=O)—O—, —C(=O)—NH—, —NH—C(=O)—, $—NH—S(=O)_2—$, $—S(=O)_2—NH—$, —O—C(=O)—NH—, —NH—C(=O)—O—, —NH—C(=O)—NH—, $—O—C_6H_4—$, $—NH—C_6H_4—$, $—O—(CH_2)_m—O—$, $—NH—(CH_2)_m—NH—$, $—O—(CH_2)_m—NH—$, $—NH—(CH_2)_m—O—$, $—O—(CH_2)_m—O—C(=O)—$, $—O—(CH_2)_m—C(=O)—O—$, $—NH—(CH_2)_m—O—C(=O)—$, $—NH—(CH_2)_m—C(=O)—O—$, $—O—(CH_2)_m—O—C(=O)—NH—$, $—O—(CH_2)_m—NH—C(=O)—O—$, $—O—(CH_2)_m—C(=O)—NH—$, $—O—(CH_2)_m—NH—C(=O)—$, $—O—(CH_2)_m—NH—C(=O)—NH—$, $—O—(CH_2)_m—O—C_6H_4—$, $—NH—(CH_2)_m—O—C(=O)—NH—$, $—NH—(CH_2)_m—NH—C(=O)—O—$, $—NH—(CH_2)_m—C(=O)—NH—$, $—NH—(CH_2)_m—NH—C(=O)—$, $—NH—(CH_2)_m—NH—C(=O)—NH—$, $—NH—(CH_2)_m—O—C_6H_4—$, $—NH—(CH_2)_m—NH—C_6H_4—$, wherein m is an integer of 1 to 5.

$Y^2$ is preferably —O—, —NH—, —O—C(=O)—, —C(=O)—O—, —C(=O)—NH—, —NH—C(=O)—, $—NH—S(=O)_2—$, $—S(=O)_2—NH—$, —O—C(=O)—NH—, —NH—C(=O)—O—, —NH—C(=O)—NH— or $—O—C_6H_4—$. $Y^2$ is more preferably —NH—C(=O)—, —C(=O)—NH—, —O—C(=O)—NH—, —NH—C(=O)—O— or —NH—C(=O)—NH—.

At least one of $Y^1$ and $Y^2$ preferably has an amide group. In other words, when $Y^1$ is not a NH group, $Y^2$ preferably has an amide group, and, when $Y^2$ has no amide group, $Y^1$ is preferably a NH group.

Z is a direct bond or a divalent or trivalent hydrocarbon group having 1 to 6 carbon atoms (for example, 1 to 5, 1 to 4, or 1 to 3) and may have a straight-chain structure or a branched structure. The number of carbon atoms in Z is preferably 2 to 4 and particularly 2. Specific examples of Z are a direct bond, $—CH_2—$, $—CH_2CH_2—$, $—CH_2CH_2CH_2—$, $—CH_2CH_2CH_2CH_2—$, $—CH_2CH_2CH_2CH_2CH_2—$, $—CH_2CH=$having a branched structure, $—CH_2(CH—)CH_2—$ having a branched structure, $—CH_2CH_2CH=$having a branched structure, $—CH_2CH_2CH_2CH_2CH=$having a branched structure, $—CH_2CH_2(CH—)CH_2—$ having a branched structure and $—CH_2CH_2CH_2CH=$having a branched structure.

Z may not be a direct bond, and $Y^2$ and Z may not be direct bonds at the same time.

The amide monomer (a1) is preferably $CH_2=C(—X^5)—C(=O)—O—(CH_2)_m—NH—C(=O)—R^3$, $CH_2=C(—X^5)—C(=O)—O—(CH_2)_mO—C(=O)—NH—R^3$, $CH_2=C(—X^5)—C(=O)—O—(CH_2)_m—NH—C(=O)—O—R^3$, $CH_2=C(—X^5)—C(=O)—O—(CH_2)_m—NH—C(=O)—NH—R^3$, wherein $R^3$ and $X^5$ have the same meaning as described above.

The amide monomer (a1) is particularly preferably $CH_2=C(—X^5)—C(=O)—O—(CH_2)_m—NH—C(=O)—R^3$.

The amide monomer (a1) can be produced by reacting a hydroxy group-containing (meth)acrylate or a hydroxy group-containing (meth)acrylamide (for example, hydroxyalkyl (meth)acrylate or hydroxyalkyl (meth)acrylamide) or an amino group-containing (meth)acrylate or an amino group-containing (meth)acrylamide (for example, aminoalkyl (meth)acrylate or aminoalkyl (meth)acrylamide) with a long-chain alkyl isocyanate. Examples of the long-chain alkyl isocyanate include lauryl isocyanate, myristyl isocyanate, cetyl isocyanate, stearyl isocyanate, oleyl isocyanate, behenyl isocyanate and the like.

Alternatively, the amide monomer (a1) can be produced by reacting a (meth)acrylate having an isocyanate group at a side chain, for example, 2-methacryloyloxyethyl methacrylate with a long-chain alkylamine or a long-chain alkyl alcohol. Examples of the long-chain alkylamine include laurylamine, myristylamine, cetylamine, stearylamine, oleylamine, behenylamine and the like. Examples of the long-chain alkyl alcohol include lauryl alcohol, myristyl alcohol, cetyl alcohol, stearyl alcohol, oleyl alcohol, behenyl alcohol and the like.

As the amide monomer (a1), the following structures can be exemplified:

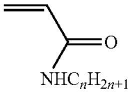

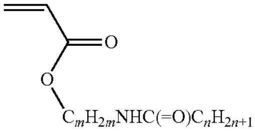

-continued

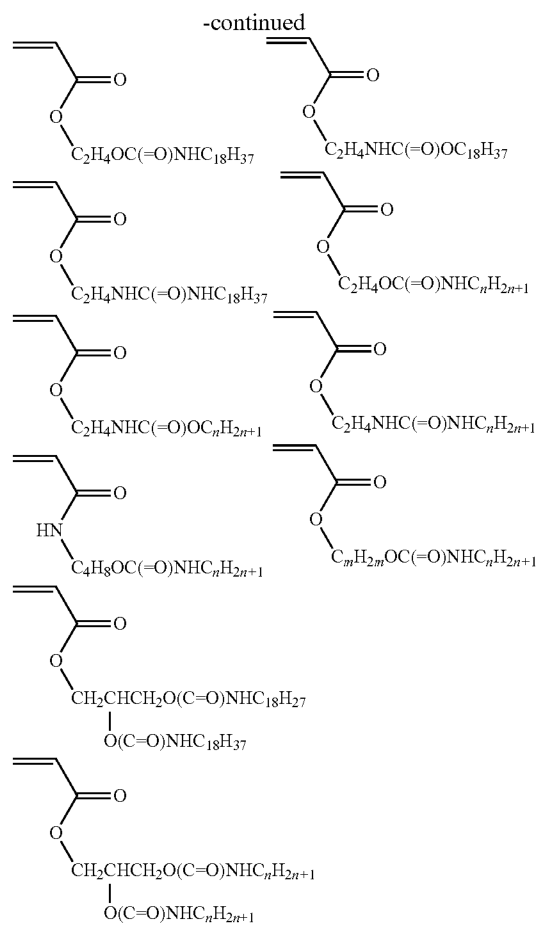

wherein n is a number of 7 to 40, and m is a number of 1 to 5.

The compounds of the above chemical formulae are acrylic compounds, which has a hydrogen atom on the α position; however, specific examples may be a methacryl compound, which has a methyl group on the α position and an α chloroacryl compound, which has a chlorine atom on the α position.

Specific examples of the amide monomer (a) include alkyl acrylamides such as stearyl (meth)acrylamide, icosyl (meth) acrylamide and behenyl (meth)acrylamide; carboxylic acid amidoalkyl (meth)acrylates such as palmitic acid amidoethyl (meth)acrylate, stearic acid amidoethyl (meth)acrylate, behenic acid amidoethyl (meth)acrylate, myristric acid amidoethyl (meth)acrylate, lauric acid amidoethyl (meth)acrylate, isostearic acid ethylamide (meth)acrylate, oleic acid ethylamide (meth)acrylate, tertiary butylcyclohexylcaproic acid amidoethyl (meth)acrylate, adamantan carboxylic acid ethylamide (meth)acrylate, naphthalene carboxylic acid amidoethyl (meth)acrylate, anthracene carboxylic acid amidoethyl (meth)acrylate, palmitic acid amidopropyl (meth) acrylate and stearic acid amidopropyl (meth)acrylate; and mixtures thereof. The amide monomer (a) is preferably stearic acid amidoethyl (meth)acrylate. The amide monomer (a) is preferably a carboxylic acid amidoalkyl (meth)acrylate and may be, particularly, a mixture containing stearic acid amidoethyl (meth)acrylate. In the mixture containing stearic acid amidoethyl (meth)acrylate, the amount of stearic acid amidoethyl (meth)acrylate may be, for example, 55% to 99% by weight, preferably 60% to 85% by weight and more preferably 65% to 80% by weight with respect to the weight of the entire amide monomer (a), and the remaining monomer may be, for example, palmitic acid amidoethyl (meth) acrylate.

The melting point of the amide monomer (a1) having a long-chain hydrocarbon group is preferably 10° C. or higher and more preferably 25° C. or higher.

Non-Amide Monomer (a2)

The non-amide monomer (a2) has a long-chain hydrocarbon group and has no amide group. The long-chain hydrocarbon group is as described above.

The non-amide monomer (a2) is a compound represented by a formula:

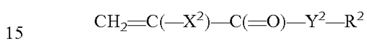

$$CH_2{=}C(-X^2)-C({=}O)-Y^2-R^2$$

wherein $R^2$ is a hydrocarbon group having 7 to 40 carbon atoms, $X^2$ is a hydrogen atom, a monovalent organic group or a halogen atom, and $Y^2$ is —O—.

The non-amide monomer (a2) may be a long-chain acrylate ester monomer in which $Y^2$ is —O—.

$R^2$ is a long-chain hydrocarbon group and, preferably an aliphatic hydrocarbon group, especially preferably a saturated aliphatic hydrocarbon group and, particularly preferably an alkyl group. The number of carbon atoms in the long-chain hydrocarbon group may be 7 or more, 10 or more, 12 or more, 14 or more, 16 or more, 18 or more or 20 or more and is preferably 10 or more or 12 or more. The number of carbon atoms in the long-chain hydrocarbon group may be 40 or less, 35 or less, 30 or less, 25 or less, 22 or less, 20 or less or 18 or less. The number of carbon atoms is preferably 30 or less.

$X^2$ may be a hydrogen atom, a methyl group, a halogen excluding a fluorine atom, a substituted or unsubstituted benzyl group or a substituted or unsubstituted phenyl group. A hydrogen atom, a methyl group or a chlorine atom is preferable.

Preferable specific examples of the non-amide monomer (a2) are lauryl (meth)acrylate, stearyl (meth)acrylate, icosyl (meth)acrylate, behenyl (meth)acrylate, stearyl α-chloroacrylate, icosyl α-chloroacrylate, behenyl α-chloroacrylate and the like.

(Hydrophilic Group-Containing Monomer (b))

A hydrophilic group-containing monomer (b) is an acrylic monomer having a hydrophilic group. The hydrophilic group-containing monomer (b) is a monomer different from the amide monomer (a), and the hydrophilic group is preferably an oxyalkylene group (the number of carbon atoms in the alkylene group is 2 to 6). Particularly, the hydrophilic group-containing monomer (b) is preferably polyalkylene glycol mono(meth)acrylate and/or polyalkylene glycol di(meth)acrylate, polyalkylene glycol mono(meth)acrylamide, hydroxyethyl acrylate, hydroxypropyl acrylate, hydroxybutyl acrylate or hydroxyethyl acrylamide.

[Monomer (c) Having Ion Donor Group]

The monomer (c) having an ion donor group is preferably a monomer having an olefinic carbon-carbon double bond and an ion donor group. As the ion donor group, there are an anion donor group and/or a cation donor group.

Examples of a monomer having an anion donor group include monomers having a carboxyl group, a sulfonic acid group or a phosphoric acid group. Specific examples of the monomer having an anion donor group are (meta)acrylic acids, crotonic acid, maleic acid, fumaric acid, itaconic acid, citraconic acid, vinylsulfonic acid, (meth)allylsulfonic acid, styrene sulfonic acid, phosphoric acid (meth)acrylate, vinyl benzene sulfonic acid, acrylamido-tertiary-butyl sulfonic acid and the like or salts thereof.

Examples of salts of the anion donor group include alkaline metal salts, alkaline earth metal salts, or ammonium salts, for example, methylammonium salts, ethanolammonium salts, triethanolammonium salts and the like.

For monomers having a cation donor group, examples of the cation donor group are amino groups, preferably, a tertiary amino group and a quaternary amino group. In the tertiary amino group, two groups bonding to a nitrogen atom are the same or different from each other and are preferably aliphatic groups having 1 to 5 carbon atoms (particularly, an alkyl group), aromatic groups having 6 to 20 carbon atoms (aryl group) or araliphatic groups having 7 to 25 carbon atoms (particularly, an aralkyl group, for example, a benzyl group ($C_6H_5$—$CH_2$—)). In the quaternary amino group, three groups bonding to a nitrogen atom are the same or different from each other and are preferably aliphatic groups having 1 to 5 carbon atoms (particularly, an alkyl group), aromatic groups having 6 to 20 carbon atoms (aryl group) or araliphatic groups having 7 to 25 carbon atoms (particularly, an aralkyl group, for example, a benzyl group ($C_6H_5$—$CH_2$—)). In the tertiary amino group and the quaternary amino group, one remaining group bonding to the nitrogen atom may have a carbon-carbon double bond. The cation donor group may have a salt form.

The cation donor group in the form of a salt is a salt with an acid (an organic acid or an inorganic acid). The organic acid is preferably, for example, a carboxylic acid having 1 to 20 carbon atoms (particularly, a monocarboxylic acid such as acetic acid, propionic acid, butyric acid or stearic acid). Dimethylaminoethyl (meth)acrylate, diethylaminoethyl (meth)acrylate and salts thereof are preferable.

(Further Monomer (d))

The further monomer (d) is a monomer other than the monomers (a), (b) or (c). Examples of such a further monomer include ethylene, vinyl acetate, vinyl chloride, vinyl fluoride, halogenated vinyl styrene, α-methylstyrene, p-methylstyrene, polyoxyalkylene mono(meth)acrylate, (meth)acrylamide, diacetone (meth)acrylamide, methylolated (meth)acrylamide, N-methylol (meth)acrylamide, alkyl vinyl ether, halogenated alkyl vinyl ether, alkyl vinyl ketone, butadiene, isoprene, chloroprene, glycidyl (meth) acrylate, aziridinyl (meth)acrylate, benzyl (meth)acrylate, isocyanateethyl (meta)acrylate, cyclohexyl (meth)acrylate, isobornyl (meth)acrylate, short-chain alkyl (meth)acrylate, maleic anhydride, (meth)acrylates having a polydimethylsiloxane group and N-vinylcarbazole.

The above-described monomers (a) to (d) may not have a fluoroalkyl group having one or more, three or more, six or more or eight or more carbon atoms (particularly, a perfluoroalkyl group). The above-described monomers (a) to (d) may not have a fluorine atom.

(Composition and Others of Graft Polymer)

The weight ratio of the branch moiety (aliphatic hydrocarbon group-containing polymer) to the total of the trunk moiety (bio-based material) and the branch moiety may be 1% by weight or more, 5% by weight or more, 10% by weight or more, 30% by weight or more, 50% by weight or more, 70% by weight or more or 90% by weight or more. The weight ratio of the branch moiety (aliphatic hydrocarbon group-containing polymer) to the total of the trunk moiety (bio-based material) and the branch moiety may be 95% by weight or less, 85% by weight or less, 75% by weight or less, 65% by weight or less, 45% by weight or less, 35% by weight or less, 25% by weight or less or 15% by weight or less.

The amount of the repeating unit that is formed of the monomer (a) (repeating unit (a)) may be 20% by weight or more, 30% by weight or more, 40% by weight or more, 45% by weight or more, 50% by weight or more, 60% by weight or more or 75% by weight or more with respect to the polymer (or the total of the repeating units (a) to (d)). The amount of the repeating unit that is formed of the monomer (a) (repeating unit (a)) may be 95% by weight or less, 75% by weight or less, 60% by weight or less or 50% by weight or less with respect to the polymer (or the total of the repeating units (a) to (d)).

The amount of the repeating unit that is formed of the monomer (a1) (repeating unit (a1)) may be 10% by weight or more, 15% by weight or more, 20% by weight or more, 25% by weight or more, 30% by weight or more, 40% by weight or more, 50% by weight or more or 60% by weight or more with respect to the polymer (or the total of the repeating units (a) to (d)). The amount of the repeating unit that is formed of the monomer (a1) (repeating unit (a1)) may be 95% by weight or less, 75% by weight or less, 60% by weight or less, 50% by weight or less, 40% by weight or less or 30% by weight or less with respect to the polymer (or the total of the repeating units (a) to (d)).

The amount of the repeating unit that is formed of the monomer (b) (repeating unit (b)) may be 0.1% by weight or more, 1% by weight or more, 3% by weight or more, 5% by weight or more, 10% by weight or more, 20% by weight or more or 30% by weight or more with respect to the polymer (or the total of the repeating units (a) to (d)). The amount of the repeating unit that is formed of the monomer (b) (repeating unit (b)) may be 75% by weight or less, 60% by weight or less, 50% by weight or less, 40% by weight or less, 30% by weight or less, 20% by weight or less, 10% by weight or less or 5% by weight or less with respect to the polymer (or the total of the repeating units (a) to (d)).

The amount of the repeating unit that is formed of the monomer (c) (repeating unit (c)) may be 0.1% by weight or more, 1% by weight or more, 3% by weight or more, 5% by weight or more, 10% by weight or more, 20% by weight or more or 30% by weight or more with respect to the polymer (or the total of the repeating units (a) to (d)). The amount of the repeating unit that is formed of the monomer (c) (repeating unit (c)) may be 75% by weight or less, 60% by weight or less, 50% by weight or less, 40% by weight or less, 30% by weight or less, 20% by weight or less, 10% by weight or less or 5% by weight or less with respect to the polymer (or the total of the repeating units (a) to (d)).

The amount of the repeating unit that is formed of the monomer (d) (repeating unit (d)) may be 0.1% by weight or more, 1% by weight or more, 3% by weight or more, 5% by weight or more, 10% by weight or more, 20% by weight or more or 30% by weight or more with respect to the polymer (or the total of the repeating units (a) to (d)). The amount of the repeating unit that is formed of the monomer (d) (repeating unit (d)) may be 50% by weight or less, 40% by weight or less, 30% by weight or less, 20% by weight or less, 10% by weight or less or 5% by weight or less with respect to the polymer (or the total of the repeating units (a) to (d)).

The weight-average molecular weight of the branch moiety (long-chain hydrocarbon group-containing polymer) of the graft polymer may be 1,000 or more, 3,000 or more, 5,000 or more, 7,500 or more, 10,000 or more or 30,000 or more. The weight-average molecular weight of the polymer may be 10,000,000 or less, 5,000,000 or less, 1,000,000 or less, 500,000 or less, 3,000,000 or less or 100,000 or less. The weight-average molecular weight is a value, in terms of polystyrene, obtained by gel permeation chromatography.

[Method for Producing Polymer]

A method for producing the polymer in the present disclosure preferably includes a step of graft-modifying a bio-based material with a polymer having a long-chain hydrocarbon group and an amide group. For example, it is possible to use a Grafting-to method, a Grafting-from method or the like, which are well known to persons skilled in the art. Regarding graft polymerization, a textbook "Principles of Polymerization" (G. G. Odian, Wiley Interscience, 1991, 3rd edition, pp. 715 to 725) or the like can be referred to.

For example, a graft polymer may be obtained by a method including first polymerizing the long-chain hydrocarbon group-containing polymer as the branch moiety, and chemically bonding the obtained polymer to the bio-based material as the trunk moiety. A method for chemically bonding the polymer to the bio-based material is not limited, and it is possible to use an etherification reaction, an acylation reaction (esterification or amidation), a reaction involving use of an epoxy group, or a reaction involving use of an isocyanate. In this case, the bio-based material and the long-chain hydrocarbon group-containing polymer each need to have a reactive group for bonding to each other. For example, a hydroxy group in the bio-based material and a carboxylic acid group in the long-chain hydrocarbon group-containing polymer may be reacted with each other. In order to progress the reaction, a reaction catalyst or the like may be used as appropriate.

For example, a functional group in the trunk moiety may be used as a polymerization initiation group, and a graft chain as a branch moiety may be grown from the polymerization initiation group. In this method, the graft polymer may be obtained by polymerizing the monomers in the presence of the bio-based material. In this method, an active site (particularly, a free radical) may be formed at a side chain of the bio-based material, and the polymerization of the monomers (a) to (d) can then progress from the active site. The formation of the active site may be caused by a chain transfer reaction in the polymerization process of the monomers. The graft polymer may also be obtained by bonding a radical reaction terminal of the polymer and the active site. This method may also be used in a bio-based material including a hydroxy group (for example, a secondary alcohol).

In order to obtain the long-chain hydrocarbon group-containing polymer, a variety of polymerization methods such as solution polymerization, emulsion polymerization and radiation induced polymerization can be selected. For example, the polymerization method may be solution polymerization in which water or an organic solvent is used, suspension polymerization in which an organic solvent and water are used in combination, or emulsion polymerization in which a surfactant is used or self-dispersion type emulsion polymerization. Graft modification is carried out in the presence of the bio-based material and is preferably carried out under a condition that the bio-based material is dispersed (preferably dissolves).

A method for producing the long-chain hydrocarbon group-containing polymer in the present disclosure preferably includes a step of polymerizing the above-described monomers in the presence of the bio-based material. This production method gives a polymer-containing composition containing the long-chain hydrocarbon group-containing polymer; a cluster of the long-chain hydrocarbon group-containing polymer and the bio-based material; and/or a mixture of the long-chain hydrocarbon group-containing polymer and the bio-based material. The polymer or polymer-containing composition obtained by this production method can have excellent oil-resisting performance.

Examples of a polymerization initiator used include water-soluble polymerization initiators, such as 2,2'-azobisisobutylamidine dihydrochloride, 2,2'-azobis(2-methylpropionamidine) hydrochloride, 2,2'-azobis[2-(2-imidazolin-2-yl)propane]hydrochloride, 2,2'-azobis[2-(2-imidazolin-2-yl) propane]sulfate hydrate, 2,2'-azobis[2-(5-methyl-2-imidazolin-2-yl)propane] hydrochloride, potassium persulfate, barium persulfate, ammonium persulfate and hydrogen peroxide; and oil-soluble polymerization initiators, such as 2,2'-azobis(2-methylpropionitrile), 2,2'-azobis (2-methylbutyronitrile), 2,2'-azobis(2,4-dimethylvaleronitrile), 2,2'-azobis(2,4-dimethyl 4-methoxyvaleronitrile), 1,1'-azobis(cyclohexan-1-carbonitrile), dimethyl 2,2'-azobis (2-methylpropionate), 2,2'-azobis(2-isobutyronitrile), benzoyl peroxide, di-tertiary-butyl peroxide, lauryl peroxide, cumene hydroperoxide, t-butyl peroxypivalate, diisopropyl peroxydicarbonate, and t-butyl peroxypivalate. The initiator may be an oxidant initiator, a reducing agent initiator or a redox initiator and may include, for example, a combination of a peroxide and a reducing agent, a combination of an inorganic reducing agent and an oxidant or an inorganic-organic redox pair. As the initiator, a polyvalent ion selected from $Ce^{4+}$, $V^{5+}$, $Cr^{6+}$ and $Mn^{3+}$ may be used. The initiator may be used in a range of 20 parts by weight or less, for example, 0.01 to 15 parts by weight, 0.01 to 10 parts by weight or 0.01 to 5 parts by weight, with respect to 100 parts by weight of the monomers.

For the purpose of adjusting the molecular weight, a chain transfer agent, for example, a mercapto group-containing compound may also be used, and specific examples thereof include 2-mercaptoethanol, thiopropionic acid, alkyl mercaptan and the like. The chain transfer agent may be used in a range of 10 parts by weight or less, for example, 0.01 to 5 parts by weight, with respect to 100 parts by weight of the monomers.

<Oil-Resistant Agent>

The oil-resistant agent is an oil-resistant agent containing the above-described graft polymer. The oil-resistant agent has oil resistance and may further have water resistance, water-repellency and oil-repellency. The oil-resistant agent may contain, in addition to the graft polymer, a liquid medium (water, an organic solvent or a mixed solution thereof). The oil-resistant agent may further contain at least one selected from a surfactant, other additives and the like.

The amount of the graft polymer may be 0.1% by weight or more, 1% by weight or more, 3% by weight or more, 5% by weight or more, 10% by weight or more, 20% by weight or more or 50% by weight or more with respect to the oil-resistant agent. The amount of the graft polymer may be 100% by weight or less, 75% by weight or less, 50% by weight or less or 25% by weight or less with respect to the oil-resistant agent.

The oil-resistant agent may contain a liquid medium. The liquid medium is pure water, a pure organic solvent or a mixture of water and an organic solvent and is preferably pure water or a mixture of water and an organic solvent.

The amount of the liquid medium may be 30% by weight or more, 50% by weight or more, 60% by weight or more, 75% by weight or more or 90% by weight or more with respect to the oil-resistant agent. The amount of the liquid medium may be 95% by weight or less, 75% by weight or less or 50% by weight or less with respect to the oil-resistant agent.

In a case where the liquid medium is a mixture of water and an organic solvent, the amount of the organic solvent may be 3% by weight or more, 10% by weight or more, 30% by weight or more, 50% by weight or more or 75% by weight or more with respect to the liquid medium. The amount of the organic solvent may be 90% by weight or less, 50% by weight or less, 30% by weight or less or 10% by weight or less with respect to the liquid medium.

[Surfactant or Dispersant]

The oil-resistant agent may not contain or may contain a surfactant (emulsifier) or a dispersant. Ordinarily, in order for the stabilization of particles during polymerization or the stabilization of a water dispersion after polymerization, a small amount (for example, 0.01 to 45 parts by weight, 0.01 to 30 parts by weight or 0.01 to 15 parts by weight with respect to 100 parts by weight of the total amount of the bio-based material and the monomer or 100 parts by weight of the graft polymer) of a surfactant or a dispersant may be added at the time of polymerization or a surfactant or a dispersant may be added after polymerization.

Particularly, in a case where a treatment target is a fiber product, the oil-resistant agent preferably contains a nonionic surfactant as the surfactant or the dispersant. Furthermore, as the surfactant, one or more surfactants selected from a cationic surfactant, an anionic surfactant and an amphoteric surfactant are preferably contained. A combination of a nonionic surfactant and a cationic surfactant is preferably used.

Each of the nonionic surfactant, the cationic surfactant and the amphoteric surfactant may be a combination of one or more thereof.

The amount of the surfactant or the dispersant may be 45 parts by weight or less, 30 parts by weight or less, 15 parts by weight or less, 10 parts by weight or less, 7.5 parts by weight or less, 5 parts by weight or less or 2.5 parts by weight or less with respect to 100 parts by weight of the total amount of the bio-based material and the monomer or the graft polymer. The amount of the surfactant or the dispersant may be 0.1 parts by weight or more, 1 part by weight or more, 3 parts by weight or more, 5 parts by weight or more, 7.5 parts by weight or more or 10 parts by weight or more with respect to 100 parts by weight of the total amount of the bio-based material and the monomer or the graft polymer. Ordinarily, when the surfactant or the dispersant is added, the stability or permeability into fiber products of a water dispersion improves.

[Blocked Isocyanate Compound]

The oil-resistant agent may not contain or may contain a blocked isocyanate compound. The blocked isocyanate compound may be added before polymerization or may be added after polymerization (for example, before a curing step after polymerization).

The blocked isocyanate compound can be produced by reacting isocyanate (which may be a compound represented by $A(NCO)_m$, wherein A is a group remaining after an isocyanate group is removed from the isocyanate compound, and m is an integer of 2 to 8) with a blocking agent (which may be a compound represented by RH, wherein R may be a hydrocarbon group that may be substituted by a hetero atom such as a nitrogen atom or an oxygen atom, and H is a hydrogen atom).

$A(NCO)_m$ is, for example, tolylene diisocyanate (TDI), diphenylmethane diisocyanate (MDI), hexamethylene diisocyanate (HDI) or the like. Examples of the blocking agent for forming an R group is oximes, phenol, alcohols, mercaptan, amides, imides, imidazole, urea, amines, imines, pyrazole, active methylene compounds and the like.

The blocked isocyanate compound is preferably a blocked isocyanate such as oxime blocked toluene diisocyanate, blocked hexamethylene diisocyanate or blocked diphenylmethane diisocyanate.

The amount of the blocked isocyanate compound may be 15 parts by weight or less, 10 parts by weight or less, 7.5 parts by weight or less, 5 parts by weight or less or 2.5 parts by weight or less with respect to a total of 100 parts by weight of the monomers (or a total of 100 parts by weight of the polymer in the branch moiety).

[Other Additives]

The oil-resistant agent may also contain other additives. Examples of the other additives are a binder resin, a dispersant, a water-resisting agent, an oil-resistant agent, a water repellent agent, an oil repellent agent, a drying rate adjuster, a cross-linking agent, a film formation agent, a compatibilizer, an antifreezing agent, a viscosity adjuster, a ultraviolet absorber, an antioxidant, a pH adjuster, an antifoaming agent, a texture modifier, a slippage modifier, an antistatic agent, a hydrophilizing agent, an antibacterial agent, a preservative, an insect repellent, a fragrant agent, a flame retarder, a sizing agent, a paper strengthening agent and the like. The amount of the other additives may be 0.1 to 20 parts by weight and, for example, 0.1 to 10 parts by weight with respect to a total of 100 parts by weight of the monomers (or a total of 100 parts by weight of the polymer in the branch moiety).

[Uses and Others of Graft Polymer]

The graft polymer can be used as a variety of agents such as an oil-resistant agent, a water-resisting agent, a water repellent agent, an oil repellent agent, a soil resistant agent, a soil release agent, a release agent or a mold release agent, or a component thereof. The graft polymer can be used as an external treatment agent (surface-treating agent) or an internal treatment agent, or a component thereof.

When a substrate is treated with the graft polymer, the graft polymer is capable of forming a surface coating structure on the surface of the substrate.

The treated target (substrate) after treatment is dried in order to develop liquid repellency, and preferably heated at, preferably, for example, a temperature of Tg of a copolymer or higher, for example, 100° C. to 200° C. When the substrate is treated at a temperature of Tg of a copolymer or higher, the surface of the substrate is coated with the copolymer, and, furthermore, side chain arrangement is induced. This makes it possible to form a surface coating structure having excellent hydrophobicity.

The surface coating structure can be formed by applying the graft polymer to the treatment target (substrate) by a conventionally well-known method and thereby attaching the copolymer to the surface of the substrate. Normally, a method is employed in which the graft polymer is dispersed in an organic solvent or water to be diluted, attached to the surface of the treatment target by a well-known method such as immersion application, spray application or foam application and dried. In addition, if necessary, the graft polymer may be applied with an appropriate cross-linking agent (for example, a blocked isocyanate compound) and cured. Furthermore, it is also possible to add, to the graft polymer, an insect repellent, a softening agent, an antibacterial agent, a flame retarder, an antistatic agent, a coating material-fixing agent, a wrinkle-resistant agent, a sizing agent, a paper strengthening agent or the like, for combination use.

Examples of treatment targets to be treated with an agent containing the graft polymer include fiber products, stone materials, filters (for example, electrostatic filters), dust masks, fuel cell components (for example, gas diffusion electrodes and gas diffusion supports), glass, wood, leather, fur, asbestos, bricks, cement, metals and oxides, ceramic products, plastics, coated surfaces, plasters and the like.

As fiber products, as fiber products, a variety of examples can be mentioned, and examples thereof include fabric products and paper products.

Examples of fabric products include animal or plant-based natural fibers such as cotton, hemp, wool and silk, synthetic fibers such as polyamide, polyester, polyvinyl alcohol, polyacrylonitrile, polyvinyl chloride and polypropylene, semi-synthetic fibers such as rayon and acetate, inorganic fibers such as glass fibers, carbon fibers and asbestos fibers, or fiber mixtures thereof. Woven fabric, knit fabric, nonwoven fabric, clothing-form fabric and carpets are included in fabric products, and treatment may also be carried out on fibers, threads and intermediate fiber products (for example, sliver, rove and the like), which are to be processed into fabric.

Examples of paper products include bleached or unbleached chemical pulp such as kraft pulp or sulfite pulp, bleached or unbleached high-yield pulp such as ground wood pulp, mechanical pulp or thermomechanical pulp, paper made of waste paper pulp such as newspaper waste paper, magazine waste paper, cardboard waste paper or deinked waste paper or the like, container made of paper, molded bodies made of paper and the like. Specific examples of paper products include food packaging paper, gypsum board base paper, coated base paper, medium quality paper, ordinary liner and corrugating media, neutral pure white roll paper, neutral liner, rust-proof liner, metal interleaving paper, kraft paper, neutral printing/writing paper, medium coated base paper, neutral PPC paper, neutral heat-sensitive paper, neutral pressure-sensitive base paper, neutral inkjet paper, neutral information paper, molded paper (mold containers) and the like. The graft polymer of the present disclosure has excellent high-temperature oil resistance and is suitably used in uses where oil resistance at high temperatures is required, particularly, food packaging materials.

The graft polymer can be applied to fibrous substrates (for example, fiber products or the like) by any of known methods for treating fiber products with liquid. When a fiber product is fabric, the fabric may be immersed in a solution or a solution may be attached or sprayed to the fabric. The treatment may be an external sizing treatment or an internal sizing treatment. When a fiber product is paper, the graft polymer may be applied to the paper, a solution may be attached or sprayed to the paper, or a pulp slurry may be mixed and treated with the graft polymer before papermaking. The treatment may be an external sizing treatment or an internal sizing treatment.

The graft polymer may be applied to fiber products formed in advance (particularly, paper, fabric and the like) or may be applied in a variety of stages for paper manufacturing, for example, during the drying process of paper. The graft polymer may be applied to fiber products by a cleaning method and may be applied to fiber products in, for example, washing application, a dry cleaning method or the like.

The fibrous substrates may be leather. In order to make leather hydrophobic and lipophobic, a copolymer in the form of an aqueous solution or an aqueous emulsion may be applied to the leather in a variety of stages for leather processing, for example, during the wetting processing of leather or during the finishing processing of leather.

The graft polymer can also be used as an external mold release agent. For example, it is possible to peel the surface of a substrate from a different surface (a different surface in the substrate or a surface in a different substrate) easily.

"Treatment" means the application of a treatment agent to a treatment target by immersion, spraying, application or the like. The treatment allows the copolymer, which is an active component of the treatment agent, to permeate into the treatment target and/or to attach to the surface of the treatment target.

<Additive for Paper>

The graft polymer can be suitably used as an additive for paper. An additive for paper containing the graft polymer can be used as a water-resisting agent, an oil-resistant agent, a water repellent agent and an oil repellent agent. The additive for paper preferably has a form of a solution, an emulsion or an aerosol. The additive for paper contains the graft polymer and a medium (for example, a liquid medium such as an organic solvent or water). The additive for paper is preferably a water dispersion of the graft polymer. In the additive for paper, the concentration of the graft polymer may be, for example, 0.01% to 50% by weight. The additive for paper may not contain a surfactant.

The liquid medium (for example, an organic solvent or water) contained in the additive for paper can be removed by heating a polymer solution (to, for example, 30° C. or higher, for example, 50° C. to 120° C.) (preferably under reduced pressure)

The amount of the additive for paper may be an amount such that the amount, in terms of the solid content, of the graft polymer is 0.1 parts by weight or more, 0.5 parts by weight or more, 1 part by weight or more, 5 parts by weight or more, 10 parts by weight or more, 20 parts by weight or more, 30 parts by weight of more or 40 parts by weight or more with respect to 100 parts by weight of pulp. The amount of the additive for paper may be an amount such that the amount, in terms of the solid content, of the graft polymer is 100 parts by weight or less, 80 parts by weight or less, 60 parts by weight or less, 40 parts by weight or less, 20 parts by weight or less or 10 parts by weight or less with respect to 100 parts by weight of pulp. In external sizing, the amount of the graft polymer contained in an oil resistant layer may be 0.01 $g/m^2$ or more, 0.03 $g/m^2$ or more, 0.05 $g/m^2$ or more, 0.10 $g/m^2$ or more, 0.30 $g/m^2$ or more or 0.50 $g/m^2$ or more. The amount of the graft polymer contained in the oil resistant layer may be 5 $g/m^2$ or less, 3 $g/m^2$ or less, 2 $g/m^2$ or less, 1.5 $g/m^2$ or less, 0.30 $g/m^2$ or less or 0.50 $g/m^2$ or less.

The additive for paper can be used to treat paper bases (for example, a surface treatment). The additive for paper can be applied to treatment targets by conventionally well-known methods. Normally, a method is employed in which the additive for paper is dispersed in an organic solvent or water to be diluted, attached to the surface of the treatment target by a well-known method such as immersion application, spray application or foam application, and dried (surface treatment). Examples of paper bases as treatment targets include paper, container made of paper, molded bodies made of paper (for example, molded pulp) and the like. The graft polymer of the present disclosure is favorably attached to paper bases. Here, attachment refers to a physical bond or a chemical bond.

The additive for paper in the present disclosure is capable of enhancing moldability and can also be used as a moldability improver.

Hereinabove, the embodiment has been described, but it is understood that a variety of modifications in forms or details are possible without departing from the gist and scope of the claims.

EXAMPLES

Next, the present disclosure will be specifically described by way of Examples. However, the description does not limit the present disclosure. Hereinafter, "parts", "%" or "ratios" indicate "parts by weight", "% by weight" or "weight ratios" unless particularly otherwise described.

Testing methods used below are as follows.

[Biobased Content]

For the biobased content, the concentration of natural-level radiocarbon (C14) present in an organic matter that was contained in a sample was measured, and the biobased carbon (%) was used as an index. The biobased content was evaluated in accordance with ASTM D6866 standards.

[Moldability]

The moldability was evaluated by checking whether or not the graft polymer adhered to the metal mold when the graft polymer was vertically pressurized and dried on a metal male and female mold heated to 60° C. to 200° C. during making molded pulp.

x: The graft polymer adheres to the mold.

○: The graft polymer does not adhere to the mold.

[High-Temperature Oil Resistance]

100 ml of an evaluation fluid (corn oil) (80° C.) was poured into a molded pulp product in a container shape, left to stand still for 30 minutes and then disposed of, and the state of penetration of the evaluation fluid into the molded pulp product (container) was visually evaluated according to the following scale.

4: Oil stain is rarely observed on the inside of the bottom of the molded pulp container.

3: Oil stain is not observed on the outside of the bottom of the molded pulp container.

2: Oil stain is observed in less than 5% of the area of the outside of the bottom of the molded pulp container.

1: Oil stain is observed in 5% or more and less than 50% of the area of the outside of the bottom of the molded pulp container.

0: Oil stain is observed in 50% or more of the area of the outside of the bottom of the molded pulp container.

[High-Temperature Water Resistance]

100 ml of an evaluation fluid (tap water) (80° C.) was poured into a molded pulp product molded in a container shape, left to stand still for 30 minutes and then disposed of, and the state of penetration of the evaluation fluid into the molded pulp product (container) was visually evaluated according to the following scale.

4: Water stain is rarely observed on the inside of the bottom of the molded pulp container.

3: Water stain is not observed on the outside of the bottom of the molded pulp container.

2: Water stain is observed in less than 5% of the area of the outside of the bottom of the molded pulp container.

1: Water stain is observed in 5% or more and less than 50% of the area of the outside of the bottom of the molded pulp container.

0: Water stain is observed in 50% or more of the area of the outside of the bottom of the molded pulp container.

Manufacturing Example 1

60 parts of processed tapioca starch (trade name: TSK-13, product of Nihon Shokuhin Kako Co., Ltd.) was suspended in 630 parts of water under stirring in a reactor equipped with a stirrer and a heater, and the resultant was heated up to 90° C. to cause gelatinization. 6.7 parts of stearic acid amide acrylate represented by the formula $CH_2{=}CHC({=}O)OC_2H_4NHC({=}O)C_{17}H_{35}$ (C18AmEA, melting point: 70° C.) and 4.5 parts of stearyl trimethyl ammonium chloride were dissolved at 80° C., and emulsified with ultrasonic waves in the above-described gelatinized starch solution to be finely dispersed such that the average particle size of liquid droplets was 500 nm or less. Next, 1.20 parts of cerium diammonium nitrate (CAN) as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 2

68 parts of processed tapioca starch (trade name: TSK-13, product of Nihon Shokuhin Kako Co., Ltd.) was suspended in 740 parts of water under stirring in a reactor equipped with a stirrer and a heater, and the resultant was heated up to 90° C. to cause gelatinization. 11.2 parts of stearic acid amide acrylate represented by the formula $CH_2{=}CHC({=}O)\ OC_2H_4NHC({=}O)\ C_{17}H_{35}$ (C18AmEA, melting point: 70° C.) and 8.9 parts of stearyl trimethyl ammonium chloride were dissolved at 80° C., and emulsified with ultrasonic waves in the above-described gelatinized starch solution to be finely dispersed such that the average particle size of liquid droplets was 500 nm or less. Next, 1.36 parts of cerium diammonium nitrate (CAN) as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 3

60 parts of processed tapioca starch (trade name: TSK-13, product of Nihon Shokuhin Kako Co., Ltd.) was suspended in 700 parts of water under stirring in a reactor equipped with a stirrer and a heater, and the resultant was heated up to 90° C. to cause gelatinization. 15.0 parts of stearic acid amide acrylate represented by the formula $CH_2{=}CHC({=}O)\ OC_2H_4NHC({=}O)\ C_{17}H_{35}$ (C18AmEA, melting point: 70° C.) and 11.9 parts of stearyl trimethyl ammonium chloride were dissolved at 80° C., and emulsified with ultrasonic waves in the above-described gelatinized starch solution to be finely dispersed such that the average particle size of liquid droplets was 500 nm or less. Next, 1.32 parts of cerium diammonium nitrate (CAN) as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 4

68 parts of processed tapioca starch (trade name: TSK-13, product of Nihon Shokuhin Kako Co., Ltd.) was suspended in 740 parts of water under stirring in a reactor equipped with a stirrer and a heater, and the resultant was heated up to 90° C. to cause gelatinization. 11.2 parts of stearic acid amide acrylate represented by the formula $CH_2{=}CHC({=}O)\ OC_2H_4NHC({=}O)\ C_{17}H_{35}$ (C18AmEA, melting point: 70° C.) and 8.9 parts of bishydroxyethylalkyl (C8-18) methyl ammonium chloride were dissolved at 80° C., and emulsified with ultrasonic waves in the above-described gelatinized starch solution to be finely dispersed such that the average particle size of liquid droplets was 500 nm or less. Next, 1.36 parts of cerium diammonium nitrate (CAN)

as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 5

68 parts of oxidized starch (trade name: MS #3800, product of Nihon Shokuhin Kako Co., Ltd.) was suspended in 740 parts of water under stirring in a reactor equipped with a stirrer and a heater, and the resultant was heated up to 90° C. to cause gelatinization. 11.2 parts of stearic acid amide acrylate represented by the formula $CH_2{=}CHC({=}O)OC_2H_4NHC({=}O)C_{17}H_{35}$ (C18AmEA, melting point: 70° C.) and 8.9 parts of bishydroxyethylalkyl (C8-18) methyl ammonium chloride were dissolved at 80° C., and emulsified with ultrasonic waves in the above-described gelatinized starch solution to be finely dispersed such that the average particle size of liquid droplets was 500 nm or less. Next, 1.36 parts of cerium diammonium nitrate (CAN) as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 6

68 parts of cationized starch (trade name: CATOSIZE380H, product of Ingredion) was suspended in 740 parts of water under stirring in a reactor equipped with a stirrer and a heater, and the resultant was heated up to 90° C. to cause gelatinization. 11.2 parts of stearic acid amide acrylate represented by the formula $CH_2{=}CHC({=}O)OC_2H_4NHC({=}O)C_{17}H_{35}$ (C18AmEA, melting point: 70° C.) and 8.9 parts of bishydroxyethylalkyl (C8-18) methyl ammonium chloride were dissolved at 80° C., and emulsified with ultrasonic waves in the above-described gelatinized starch solution to be finely dispersed such that the average particle size of liquid droplets was 500 nm or less. Next, 1.36 parts of cerium diammonium nitrate (CAN) as an initiator was added thereto, and the resulting mixture was mixed and stirred in a nitrogen atmosphere at 60° C. for 5 hours to thereby cause polymerization. The solid content of the obtained polymer-containing solution was 10% by weight.

Manufacturing Example 7 (SHA14%, LIPOTHQUAD, V-50)

68 parts of processed tapioca starch (trade name: TSK-13, product of Nihon Shokuhin Kako Co., Ltd.) was suspended in 740 parts of water under stirring in a reactor equipped with a stirrer and a heater, and the resultant was heated up to 90° C. to cause gelatinization. 11.2 parts of stearic acid amide acrylate represented by the formula $CH_2{=}CHC({=}O)OC_2H_4NHC({=}O)C_{17}H_{35}$ (C18AmEA, melting point: 70° C.) and 8.9 parts of bishydroxyethylalkyl (C8-18) methyl ammonium chloride were dissolved at 80° C., and emulsified with ultrasonic waves in the above-described gelatinized starch solution to be finely dispersed such that the average particle size of liquid droplets was 500 nm or less. Next, 1.36 parts of azobisamidinopropane hydrochloride as an initiator was added thereto, and the resulting mixture was mixed and stirred in a nitrogen atmosphere at 60° C. for 5 hours to thereby cause polymerization. The solid content of the obtained polymer-containing solution was 10% by weight.

Comparative Manufacturing Example 1

20 parts of processed tapioca starch (trade name: TSK-13, product of Nihon Shokuhin Kako Co., Ltd.) was suspended in 180 parts of water under stirring in a reactor equipped with a stirrer and a heater, and the resultant was heated up to 90° C. to cause gelatinization, thereby obtaining a starch suspension. The solid content of the obtained starch suspension was 10% by weight.

Example 1

2,400 g of a water dispersion containing 0.5% by weight of a mixture of 70 parts of leaf bleached kraft pulp and 30 parts of northern bleached kraft pulp beaded to a freeness of 550 cc (Canadian Freeness) was added under stirring. Next, 0.18 g of an aqueous solution containing 5%, in terms of solid content, of an alkyl ketene dimer (AKD) (Hercon (registered trademark) 79, manufactured by Solenis) was added, followed by continuously stirring for 1 minute, and then 36 g of the water dispersion of the non-fluorine copolymer of Manufacturing Example 1 diluted to a solid content of 10% with water was added, followed by continuously stirring for 1 minute.

The above-described pulp slurry was put into a metal vessel. A metal mold for pulp molding with a number of suction holes was placed in the lower part of the vessel with a netlike body disposed thereon. The pulp-containing aqueous composition was suctioned and dehydrated through the mold for pulp molding and the netlike body with a vacuum pump from a side opposite to the netlike body side with respect to the mold for pulp molding, so that the solids (the pulp and the like) contained in the pulp-containing aqueous composition was deposited on the netlike body, thereby obtaining a molded pulp intermediate. Next, the obtained molded pulp intermediate was vertically pressed and dried in metal male-female molds heated to 60° C. to 200° C. Thus, a molded pulp product having a container shape was produced. Table 2 shows the ratio of the content of each component to that of the pulp in the obtained molded pulp product, and the results of evaluating the moldability, the high-temperature oil-resistance and the high-temperature water-resistance.

Example 2

A test was carried out in the same manner as in Example 1 except that 24 g of the water dispersion of the non-fluorine copolymer of Manufacturing Example 2 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Example 3

A test was carried out in the same manner as in Example 1 except that 18 g of the water dispersion of the non-fluorine copolymer of Manufacturing Example 3 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Example 4

A test was carried out in the same manner as in Example 1 except that 24 g of the water dispersion of the non-fluorine copolymer of Manufacturing Example 4 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Example 5

A test was carried out in the same manner as in Example 1 except that 24 g of the water dispersion of the non-fluorine copolymer of Manufacturing Example 5 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Example 6

A test was carried out in the same manner as in Example 1 except that 24 g of the water dispersion of the non-fluorine copolymer of Manufacturing Example 6 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Example 7

A test was carried out in the same manner as in Example 1 except that 24 g of the water dispersion of the non-fluorine copolymer of Manufacturing Example 7 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

Comparative Example 1

A test was carried out in the same manner as in Example 1 except that 60 g of the starch suspension of Comparative Manufacturing Example 1 was used instead of the water dispersion of the polymer of Manufacturing Example 1 in Example 1. Table 2 shows the ratio of the content of each component to that of the pulp in the obtained molded pulp product, and the results of evaluating the high-temperature oil-resistance and the high-temperature water-resistance.

TABLE 1

| | Manufacturing Example 1 | Manufacturing Example 2 | Manufacturing Example 3 | Manufacturing Example 4 | Manufacturing Example 5 | Manufacturing Example 6 | Manufacturing Example 7 | Comparative Manufacturing Example 1 |
|---|---|---|---|---|---|---|---|---|
| Bio-based material | Processed tapioca starch (TSK-13) | Processed tapioca starch (TSK-13) | Processed tapioca starch (TSK-13) | Processed tapioca starch (TSK-13) | Oxidized starch (MS#3800) | Cationized starch (CATOSIZE380H) | Processed tapioca starch (TSK-13) | Processed tapioca starch (TSK-13) |
| Long-chain hydrocarbon group-containing acrylic monomer (a) | C18AmEA | C18AmEA | C18AmEA | C18AmEA | C18AmEA | C18AmEA | C18AmEA | — |
| Biobased content | 96% | 95% | 92% | 95% | 95% | 95% | 95% | 99% |

TABLE 2

| | Treatment agent | Solid %/ Pulp | Water-resisting agent | Solid %/ Pulp | Moldability | High-temperature oil resistance | High-temperature water resistance |
|---|---|---|---|---|---|---|---|
| Example 1 | Manufacturing Example 1 | 30% | AKD | 0.15 | ○ | 3 | 3 |
| Example 2 | Manufacturing Example 2 | 20% | AKD | 0.15 | ○ | 4 | 4 |
| Example 3 | Manufacturing Example 3 | 15% | AKD | 0.15 | ○ | 4 | 4 |
| Example 4 | Manufacturing Example 4 | 20% | AKD | 0.15 | ○ | 4 | 4 |
| Example 5 | Manufacturing Example 5 | 20% | AKD | 0.15 | ○ | 4 | 4 |
| Example 6 | Manufacturing Example 6 | 20% | AKD | 0.15 | ○ | 3 | 4 |
| Example 7 | Manufacturing Example 7 | 20% | AKD | 0.15 | ○ | 4 | 4 |
| Comparative Example 1 | Comparative Manufacturing Example 1 | 50% | AKD | 0.15 | x | 0 | 0 |

Examples of the embodiments of the present disclosure are as described below.

[Item 1]

A graft polymer obtained by graft modification of a bio-based material with a long-chain hydrocarbon group-containing polymer having a long-chain hydrocarbon group having 7 to 40 carbon atoms.

[Item 2]

The graft polymer according to Item 1, wherein the long-chain hydrocarbon group-containing polymer has a repeating unit derived from an acrylic monomer (a) having a long-chain hydrocarbon group represented by the following formula:

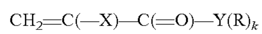

$CH_2{=}C(—X)—C({=}O)—Y(R)_k$ wherein R is each independently a hydrocarbon group having 7 to 40 carbon atoms, X is a hydrogen atom, a monovalent organic group or a halogen atom, Y is a group composed of at least one selected from a divalent to tetravalent hydrocarbon group having one carbon atom (in particular, $—CH_2—$ or $—CH{=}$), $—C_6H_4—$, $—O—$, $—C({=}O)—$, $—S({=}O)_2—$ or $—NH—$, and k is 1 to 3.

[Item 3]

The graft polymer according to Item 2, wherein the acrylic monomer (a) contains an amide monomer (a1) having at least one amide group and represented by the following formula:

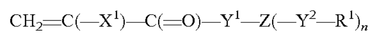

$CH_2{=}C(—X^1)—C({=}O)—Y^1—Z(—Y^2—R^1)_n$ wherein $R^1$ is each independently a long-chain hydrocarbon group having 7 to 40 carbon atoms, $X^1$ is a hydrogen atom, a monovalent organic group or a halogen atom, $Y^1$ is $—O—$ or $—NH—$, $Y^2$ is each independently a group composed of at least one selected from a direct bond, $—O—$, $—C({=}O)—$, $—S({=}O)_2—$ or $—NH—$, Z is a direct bond or a divalent or trivalent hydrocarbon group having 1 to 6 carbon atoms, and n is 1 or 2.

[Item 4]

The graft polymer according to any one of Items 1 to 3, wherein the long-chain hydrocarbon group has 12 or more carbon atoms.

[Item 5]

The graft polymer according to any one of Items 1 to 4, wherein the bio-based material is sugar.

[Item 6]

The graft polymer according to any one of Items 1 to 5, wherein the bio-based material is a polymer.

[Item 7]

The graft polymer according to any one of Items 1 to 6, wherein the graft polymer has a biobased content according to ASTM D6866 of 40% or more.

[Item 8]

An oil-resistant agent comprising the graft polymer according to any one of Items 1 to 7.

[Item 9]

The oil-resistant agent according to Item 8, wherein the oil-resistant agent is an additive for paper.

[Item 10]

A fiber product comprising the graft polymer according to any one of Items 1 to 7 attached thereto.

[Item 11]

The fiber product according to Item 10, wherein the fiber product is a paper product.

[Item 12]

The fiber product according to Item 11, wherein the paper is a food packaging material.

[Item 13]

A method for producing a long-chain hydrocarbon group-containing polymer, comprising: a step of polymerizing a monomer containing a monomer (a) in the presence of a bio-based material, wherein the monomer (a) is represented by the following formula:

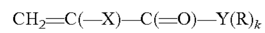

$CH_2{=}C(—X)—C({=}O)—Y(R)_k$ wherein R is each independently a hydrocarbon group having 7 to 40 carbon atoms, X is a hydrogen atom, a monovalent organic group or a halogen atom, Y is a group composed of at least one selected from a divalent to tetravalent hydrocarbon group having one carbon atom (in particular, $—CH_2—$, $—CH{=}$), $—C_6H_4—$, $—O—$, $—C({=}O)—$, $—S({=}O)_2—$ or $—NH—$, and k is 1 to 3.

[Item 14]

The producing method according to Item 13, wherein the monomer (a) is an amide monomer (a1) having at least one amide group and represented by the following formula:

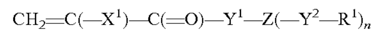

$CH_2{=}C(—X^1)—C({=}O)—Y^1—Z(—Y^2—R^1)_n$ wherein $R^1$ is each independently a long-chain hydrocarbon group having 7 to 40 carbon atoms, $X^1$ is a hydrogen atom, a monovalent organic group or a halogen atom, $Y^1$ is $—O—$ or $—NH—$, $Y^2$ is each independently a group composed of at least one selected from a direct bond, $—O—$, $—C({=}O)—$, $—S({=}O)_2—$ or $—NH—$, Z is a direct bond or a divalent or trivalent hydrocarbon group having 1 to 6 carbon atoms, and n is 1 or 2.

What is claimed is:

1. An oil-resistant agent comprising a graft polymer obtained by graft modification of a bio-based material with a long-chain hydrocarbon group-containing non-fluorine polymer having a long-chain hydrocarbon group having 7 to 40 carbon atoms, wherein the graft polymer has a biobased content according to ASTM D6866 of 40% or more, wherein the oil-resistant agent does not contain a substrate and is configured to be applied to the substrate, and wherein the oil-resistant agent is a water dispersion.

2. The oil-resistant agent according to claim 1, wherein the long-chain hydrocarbon group-containing non-fluorine polymer has a repeating unit derived from an acrylic monomer (a) having a long-chain hydrocarbon group represented by the following formula:

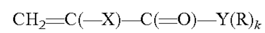

$CH_2{=}C(—X)—C({=}O)—Y(R)_k$ wherein R is each independently a hydrocarbon group having 7 to 40 carbon atoms, X is a hydrogen atom, a monovalent organic group or a halogen atom, Y is a group composed of at least one selected from a divalent to tetravalent hydrocarbon group having one carbon atom, $—C_6H_4—$, $—O—$, $—C({=}O)—$, $—S({=}O)_2—$ or $—NH—$, and k is 1 to 3.

3. The oil-resistant agent according to claim 2, wherein the acrylic monomer (a) contains an amide monomer (al) having at least one amide group and represented by the following formula:

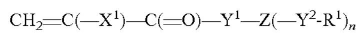

$CH_2{=}C({-}X^1){-}C({=}O){-}Y^1{-}Z({-}Y^2\text{-}R^1)_n$ wherein $R^1$ is each independently a long-chain hydrocarbon group having 7 to 40 carbon atoms, $X^1$ is a hydrogen atom, a monovalent organic group or a halogen atom, $Y^1$ is —O— or —NH—, $Y^2$ is each independently a group composed of at least one selected from a direct bond, —O—, —C(═O)—, $—S(═O)_2—$ or —NH—, at least one of $Y^1$ and $Y^2$ forms or has an amide group, Z is a direct bond or a divalent or trivalent hydrocarbon group having 1 to 6 carbon atoms, and n is 1 or 2.

4. The oil-resistant agent according to claim 1, wherein the long-chain hydrocarbon group has 12 or more carbon atoms.

5. The oil-resistant agent according to claim 1, wherein the bio-based material is sugar.

6. The oil-resistant agent according to claim 1, wherein the bio-based material is a polymer.

7. The oil-resistant agent according to claim 1, wherein the oil-resistant agent is an additive for paper.

8. A fiber product comprising the graft polymer in the oil-resistant agent according to claim 1 attached thereto.

9. The fiber product according to claim 8, wherein the fiber product is a paper product.

10. The fiber product according to claim 9, wherein the paper is a food packaging material.

11. A method for producing an oil-resistant agent comprising a long-chain hydrocarbon group-containing non-fluorine polymer, comprising:

a step of polymerizing a monomer containing a monomer (a) in the presence of a bio-based material, wherein the monomer (a) is represented by the following formula:

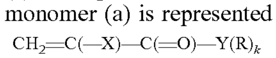

$CH_2{=}C({-}X){-}C({=}O){-}Y(R)_k$ wherein R is each independently a hydrocarbon group having 7 to 40 carbon atoms, X is a hydrogen atom, a monovalent organic group or a halogen atom, Y is a group composed of at least one selected from a divalent to tetravalent hydrocarbon group having one carbon atom, $—C_6H_4—$, —O—, —C(═O)—, $—S(═O)_2—$ or —NH—, and k is 1 to 3, wherein the long-chain hydrocarbon group-containing non-fluorine polymer is bonded to the bio-based material by graft modification to form a graft polymer, wherein the graft polymer has a biobased content according to ASTM D6866 of 40% or more, wherein the oil-resistant agent does not contain a substrate and is configured to be applied to the substrate, and wherein the oil-resistant agent is a water dispersion.

12. The method according to claim 11, wherein the monomer (a) is an amide monomer (al) having at least one amide group and represented by the following formula:

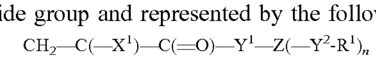

$CH_2{—}C({-}X^1){-}C({=}O){-}Y^1{-}Z({-}Y^2\text{-}R^1)_n$ wherein $R^1$ is each independently a long-chain hydrocarbon group having 7 to 40 carbon atoms, $X^1$ is a hydrogen atom, a monovalent organic group or a halogen atom, $Y^1$ is —O— or —NH—, $Y^2$ is each independently a group composed of at least one selected from a direct bond, —O—, —C(═O)—, $—S(═O)_2—$ or —NH—, Z is a direct bond or a divalent or trivalent hydrocarbon group having 1 to 6 carbon atoms, and n is 1 or 2.

* * * * *